United States Patent [19]
Kandathil et al.

[11] Patent Number: 5,948,424
[45] Date of Patent: Sep. 7, 1999

[54] COILED INSECT FUMIGANT

[75] Inventors: Thomas V. Kandathil; Francis J. Randall, both of Caledonia; James J. Runkel; Michael J. Servi, both of Mt. Pleasant, all of Wis.

[73] Assignee: S. C. Johnson & Sons, Inc., Racine, Wis.

[21] Appl. No.: 08/857,583

[22] Filed: May 16, 1997

Related U.S. Application Data

[62] Division of application No. 08/647,616, May 13, 1996, Pat. No. 5,657,574.

[51] Int. Cl.$^6$ ..................................................... A01N 25/20
[52] U.S. Cl. .......................... 424/411; 424/405; 424/407; 424/409; 424/412; 424/413; 424/DIG. 5; 424/DIG. 10; 424/40; 514/919
[58] Field of Search .............................. 424/40, 405, 407, 424/409, 411–413, DIG. 5, DIG. 10; 519/919

[56] References Cited

U.S. PATENT DOCUMENTS

| | | | |
|---|---|---|---|
| D. 329,679 | 9/1992 | Klapwald | D22/122 |
| 2,224,622 | 12/1940 | Waples | 167/40 |
| 2,606,095 | 8/1952 | Bateman et al. | 21/108 |
| 2,765,579 | 10/1956 | Gordon | 43/127 |
| 3,110,256 | 11/1963 | Barber | 102/7.2 |
| 3,314,835 | 4/1967 | White et al. | 149/23 |
| 3,623,260 | 11/1971 | Konle | 43/129 |
| 3,723,615 | 3/1973 | Okuno | 424/18 |
| 3,754,861 | 8/1973 | Sadahiro | 21/116 |
| 3,778,924 | 12/1973 | Okui | 43/129 |
| 3,796,002 | 3/1974 | Katsuda | 43/125 |
| 3,993,582 | 11/1976 | Curtis | 252/359 |
| 4,144,318 | 3/1979 | D'Orazio | 424/40 |
| 4,199,548 | 4/1980 | Kaiho et al. | 422/305 |
| 4,296,091 | 10/1981 | Joly et al. | 424/18 |
| 4,449,987 | 5/1984 | Lindauer | 44/7.5 |
| 4,693,890 | 9/1987 | Wilson et al. | 44/78 |
| 4,696,676 | 9/1987 | Wilson et al. | 44/7.5 |
| 4,750,471 | 6/1988 | Hautmann et al. | 126/43 |
| 4,756,118 | 7/1988 | Evans, III | 43/132.1 |
| 4,777,032 | 10/1988 | Barruet et al. | 424/42 |
| 4,780,286 | 10/1988 | Parent et al. | 422/125 |
| 4,839,144 | 6/1989 | Martin | 422/305 |
| 4,844,050 | 7/1989 | Hautmann et al. | 126/43 |
| 4,859,454 | 8/1989 | Barruet et al. | 424/40 |
| 4,959,925 | 10/1990 | Nelson et al. | 43/125 |
| 5,091,183 | 2/1992 | Yano et al. | 424/405 |
| 5,173,303 | 12/1992 | Lau et al. | 424/450 |
| 5,387,418 | 2/1995 | Marin et al. | 424/409 |
| 5,447,713 | 9/1995 | Eisner et al. | 424/40 |
| 5,458,882 | 10/1995 | Marin et al. | 424/411 |

FOREIGN PATENT DOCUMENTS

| | | |
|---|---|---|
| 2195403 | 3/1974 | France . |
| 2139498 | 11/1984 | United Kingdom . |
| 2276547 | 10/1994 | United Kingdom . |

*Primary Examiner*—Neil S. Levy

[57] ABSTRACT

Disclosed herein are mosquito coils having an enlarged outer portion for providing quick coverage of an insect control ingredient in a space that previously had none. The coil is provided with urea for greater breakage resistance and kerosene and peanut shell powder to improve igniting and burning characteristics.

4 Claims, 1 Drawing Sheet

COILED INSECT FUMIGANT

This is a division of application Ser. No. 08/647,616 filed on May 13, 1996, U.S. Pat. No. 5,657,574.

TECHNICAL FIELD

The present invention relates to mosquito coils and other burnable insect control ingredient delivery devices. More particularly, it provides breakage resistant fumigants that deliver a large burst of an insect control ingredient when they are initially lighted, followed by a lower, essentially steady state level thereafter.

BACKGROUND ART

Mosquito coils are coils of slowly burnable solid material that contain an insect control ingredient such as a repellent, an insecticide, or an insect growth regulator. When they burn, heat vaporizes (and thereby disperses) the insect control ingredient. Small amounts of smoke also help to disperse the insect control ingredient.

U.S. Pat. No. 5,447,713 discloses a mosquito coil having a conventional spiral configuration, and U.S. Pat. No. 3,754,861 teaches a mosquito coil having a match-like ignition tip containing potassium chloride as an oxidizer (albeit the tip does not contain any insect control ingredient). Also known are solid fumigants in certain other shapes. See e.g. U.S. Pat. No. 4,959,925.

Various compositions for such solid fumigants are known. For example, U.S. Pat. No. 4,144,318 teaches the use of allethrin, tabu powder, starches, wood powder, coco shell powder, and dye in mosquito coils, and U.S. Pat. No. 4,296,091 teaches the use of a perfume in a mosquito coil.

One drawback of prior art mosquito coils is that no provision was made to provide quick coverage for a room or other environment that previously had no insect control ingredient in it. Thus, the environment could not safely be used for an inconveniently long time.

Another drawback of the prior art coils is that they broke too easily during manufacture and handling.

A difficulty in trying to address such problems is that mosquito coils must be made so that they can be easily lit, yet they must burn at a very slow rate once lit so as to provide extended protection throughout the night. This places significant limitations on the shape and composition of mosquito coils.

It can be seen that a need exists for improved mosquito coils.

DISCLOSURE OF THE INVENTION

In one aspect the invention provides a burnable insect fumigant coil. The fumigant coil has a radially outward insect control ingredient-containing region that is linked to an insect control ingredient-containing inner coil. The inner coil extends radially inward from the radially outward region in a spiral fashion. The radially outward region has a cross-sectional area that is greater than a cross-sectional area of the inner coil which is immediately adjacent the radially outward region. The fumigant coil is configured and constituted such that upon lighting the fumigant coil at an outer end the fumigant coil can disperse insect control ingredient at a greater rate when burning through a portion of the radially outward region than when it begins burning the inner coil.

The burnable insect fumigant coil can have the radially outward region also linked to an ignition region. The ignition region can have a smaller cross-sectional area than the cross-sectional area of the radially outward region. The fumigant coil can also (or alternatively) contain kerosene to overcome any difficulties in lighting a coil with such an enlarged radially outward region.

Preferably, the fumigant coil contains urea to provide flexibility and peanut shell powder to provide for smoother burning.

Another aspect of the present invention provides a burnable insect control ingredient delivery device having an insect control ingredient, at least one burnable base material selected from the group consisting of wood powder and vegetable shell powder, and at least 0.1% urea. Preferably, the delivery device is in the shape of a coil, has at least 0.05% by weight of kerosene, at least 0.05% by weight of peanut shell powder, and 0.10% to 5.00% by weight of urea.

A further aspect of the present invention is a method of fumigating an environment. One places the above burnable insect fumigants coil in an environment and ignites it. The environment might, for example, be a bedroom of a building. It might also be the inside of a tent or an unenclosed environment.

The objects of the present invention therefore include providing a mosquito coil:

(a) having an enlarged outer portion to provide quick coverage with a repellent or another insect control ingredient;

(b) having a second coiled inner portion which has a substantially constant, lesser cross-sectional area so that fumigant waste is minimized once the room already has an adequate base concentration of fumigant dispersed in the air; and (c) which contains urea to provide flexibility.

The invention can also provide coils made of inexpensive materials, which can be inexpensively manufactured, and which do not contain environmentally unacceptable materials.

These and still other objects and advantages of the present invention (e.g., methods for using the coils) will be apparent from the description which follows. The following description is merely of the preferred embodiments. Thus, the claims should be looked to in order to understand the full scope of the invention.

BEST MODES FOR CARRYING OUT THE INVENTION

Figure 1:
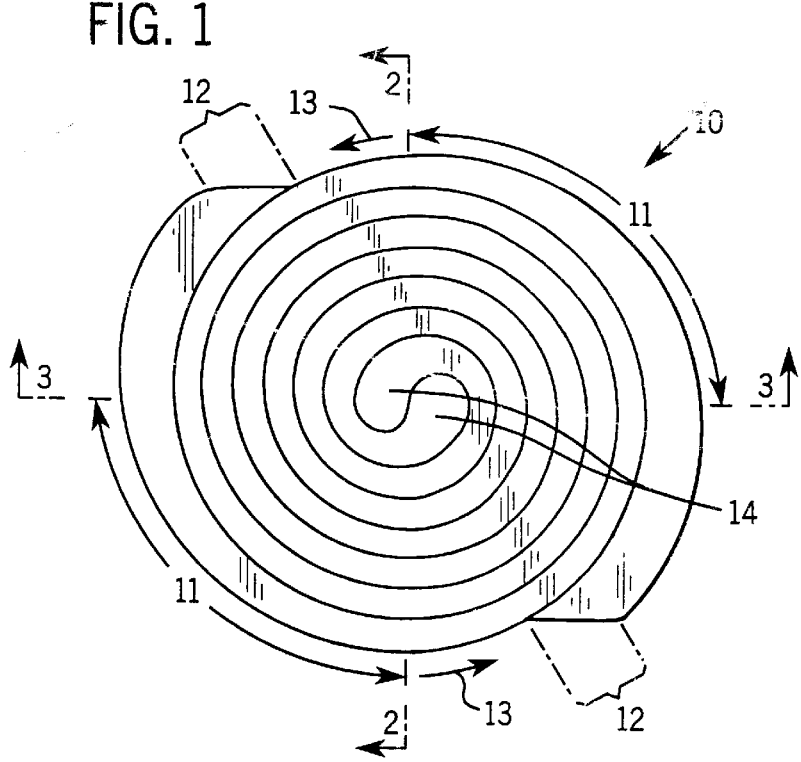
FIG. 1 is a top plan view of a preferred embodiment of the present invention.
Figure 2:
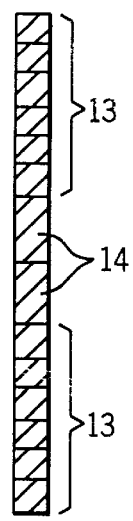
FIG. 2 is a cross-sectional view taken along line 2—2 of FIG. 1.
Figure 3:
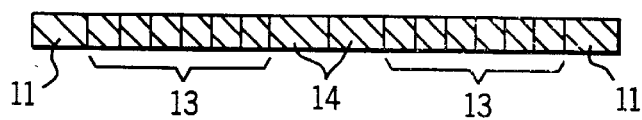
FIG. 3 is a cross-sectional view taken along line 3—3 of FIG. 1.

FIGS. 1–3 show a preferred embodiment of the present invention. In this embodiment, two mosquito coils, each a spiral in shape, are nested one within the other.

A radially outward region 11 of each fumigant coil has a steadily decreasing cross-sectional area, as one moves inwardly from the outward end of the radially outward region. An ignition region 12 is provided at the outward end of the radially outward region 11. After lighting the ignition region 12 of a fumigant coil, the radially outward region 11 burns so as to provide quick coverage of a room or other environment with an insect control ingredient such as a repellent. The ignition region 12 is adapted to light readily by a reduction of size, the inclusion of conventional oxidants, or the like. Preferably, the ignition region 12 is tapered to assist in the ignition of the fumigant coil.

Inner coil 13 extends unitarily from the innermost end of the radially outward region 11. The inner coil 13 has a substantially uniform cross-sectional area along its length. As inner coil 13 burns it minimizes waste by dispersing a lower, but essentially constant amount of insect control ingredient, when compared to the dispersion rate of the burning radially outward region 11. The burn rate of the inner coil is essentially linear. The concentration of the insect control ingredient present in the air of an enclosed area can remain high for extended periods after the initial build-up.

The radially outward region 11 of each coil preferably has two to five times greater cross-sectional area than the steady state cross-sectional area of the inner coil 13. The inner coil 13 can terminate in an enlarged area 14 so as to provide support for a conventional coil stand (not shown). Preferably, the various regions of the coil smoothly merge into each other, without abrupt changes in size.

The fumigant of FIGS. 1–3 is designed so that the two coil spirals may be separated from each other prior to use, by pulling them apart. It should be understood that portions 11, 12, 13 and 14 may have any cross-sectional geometry, including circular, elliptical, oval, rectangular, triangular, etc., or any combination thereof. It is instead the relative size of the cross-sectional areas which is important.

Figure 4:
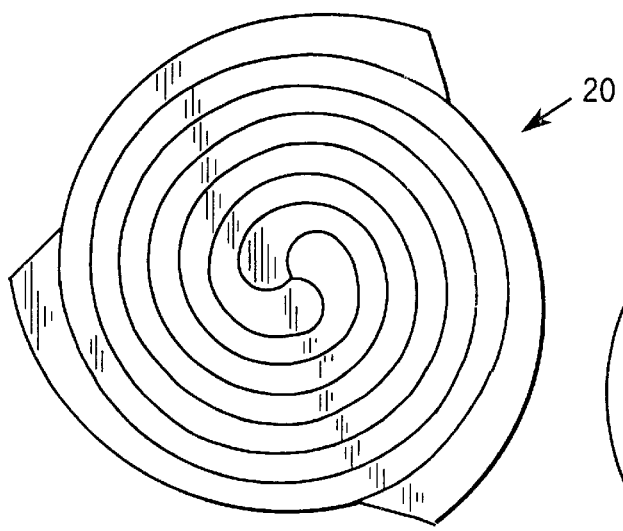
FIG. 4 is a top plan view of a second embodiment of the present invention.

FIG. 4 shows a second version 20 of the present invention that is similar to the FIG. 1 embodiment except that a third spiral is provided that is nested within two other spirals.

Figure 5:
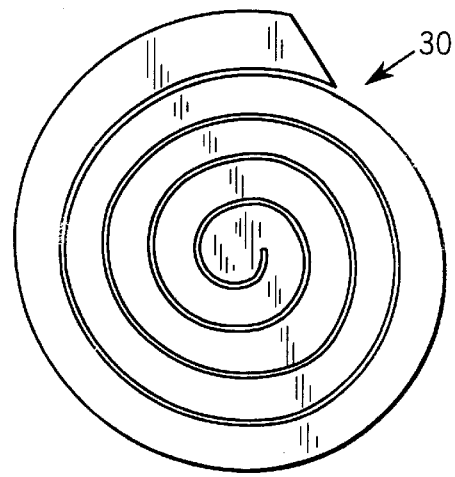
FIG. 5 is a top plan view of a third embodiment of the present invention.

FIG. 5 shows a third version 30 of the present invention that has just a single spiral. Note that when manufacturing this coil, a gap is left between each spiral "ring" to prevent the coil from burning straight towards the center (instead of around the coil).

A related aspect of the present invention is the inclusion of urea in the composition from which the coil is formed:

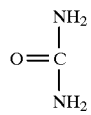

so that the coil is much more flexible. Surprisingly, the applicants have learned that the addition of urea adds sufficient flexibility to the coil to reduce the rate of coil breakage during manufacture, handling, and use, without introducing unacceptable odor or burning characteristics. The urea is preferably between 0.10% and 5.0% by weight of the composition. Most preferably, the urea comprises 0.80% by weight of the composition. An example formulation is:

| Material | Wt. % | Wt. % Range |
|---|---|---|
| Pynamin Forte (allethrin) | 0.22 | 0.05–2.0 |
| Deodorized Kerosene | 1.00 | 0.05–5.0 |
| Tabu Powder (Jiket)-Sticky Powder | 4.00 | 1.00–40.0 |
| Starch | 20.00 | 1.00–40.0 |
| Wood Powder (sawdust) | 5.00 | 1.00–50.0 |
| Coco Shell Powder | 35.00 | 1.00–50.0 |
| Peanut Shell Powder | 33.28 | 0.05–50.0 |
| Dye | 0.20 | 0.001–1.0 |
| Perfume | 0.30 | 0.01–5.00 |
| Preservative (e.g. potassium sorbate) | 0.20 | 0.01–2.00 |
| Urea | 0.80 | 0.10–5.00 |

Note in particular the use of small amounts of kerosene (preferably deodorized kerosene) and peanut shell powder. The kerosene overcomes ignition difficulties that can be caused by the enlarged radially outward region, and the peanut shell powder, due to its oily content provides smoother burning characteristics (notwithstanding the presence of the kerosene). Interestingly, even with the use of highly flammable kerosene, the coils of the present invention still have acceptably long life.

The mosquito coils of the present invention are mostly formed from a burnable "base" material. Representative materials used for the base are wood powder (e.g. sawdust), and various vegetable shell powders (e.g. coco shell; peanut shell). However, a wide variety of other slow burning materials can also form part of the base (so as to provide a coil which will last seven hours or more).

The coils of the present invention repel and/or kill flying insects which may be present in living quarters or other selected enclosed or open spaces. The coils contain an effective amount of an insect control ingredient, preferably uniformly dispersed throughout the base material. Generally, this is from 0.05–3.0% by weight of an insecticidal agent/repellent.

Traditionally, pyrethrum or pyrethroid type materials are useful in mosquito coils. Preferred pyrethroids (from the standpoint of expense and activity) are pyrethrum, resmethrin, bioallethrin, allethrin, and mixtures thereof. A particularly preferred insecticide is allethrin. Other insect control ingredients can be used such as the repellents citronella, lemon grass oil, lavender oil, cinnamon oil, neem oil, clove oil, sandlewood oil, and geraniol, and the insect growth regulator hydroprene.

The mosquito coils of the present invention may also incorporate various other burning aids which assist in sustaining the burning of the mosquito coil. Traditional and conventional burning aids can be utilized, such as sodium and potassium nitrate, and mixtures thereof. Further, other standard ingredients may be incorporated into the mosquito coil, such as dyes, pigments, perfumes, etc.

To manufacture the preferred coil, one can use a variety of techniques. In one preferred method, one first mixes the powders (other than the starch) with the dye, perfume, and preservative. These materials are blended at room temperature.

A quantity of water having a weight roughly equal to the weight of the first blended mixture is then heated. One will want to heat the water to about 150° F. (about 65.6° C.) for colder water soluble starches and to about 180° F. to 200° F. (about 82.2° C. to 93.3° C.) for hotter water soluble starch. All or a portion of the starch is slowly sifted into the water as it is heated (until the starch thickens). At this point, the urea is added to the starch/water mixture, and the material is mixed until uniform.

While one method is to add all of the starch to the heated water, alternatively only a fraction (e.g. 20%) of the starch can be thickened in this way, with the remainder of the starch being added later with the powder. Moreover, the amount of water can be varied to be more or less than equal to the weight of the non-starch powders plus dye, perfume, and preservatives. Of course, if excess water is added, it will take longer to later remove the water during the drying step discussed below.

The urea/water/starch mixture is then removed from the heat, and slowly blended in with the powder mixture to create a dough-like mass. When the mixture is essentially uniform, and only slightly warm, the insect control ingredient plus kerosene is blended in until the dough is uniform.

The dough is then preferably extruded into a ribbon sheet and cut into the desired coils. Alternatively, other techniques can be used to form the coils from the dough. After the coils are formed, they are then dried by a conventional means, such as forced air drying in a low heat oven.

It should be understood that the exact techniques for creating the coils are not critical. It is the shape and size of the coils (especially near their radial periphery), and the chemical composition of the coils, that are important for purposes of this patent.

INDUSTRIAL APPLICABILITY

The invention provides mosquito coils and other burnable insect control delivery devices. Such devices can be placed in a room or other open or closed environments, lit, and then serve to repel insects.

We claim:

1. In a burnable insect control ingredient delivery device comprising:

(a) an insect control ingredient and (b) at least one burnable base material selected from the group consisting of wood powders and vegetable shell powders; the improvement characterized by:
   the device further comprising (c) 0.1% to 5% by weight urea; and
   the device is a coil.

2. The burnable insect control ingredient delivery device of claim 1, wherein the insect control ingredient is an insect repellent.

3. The burnable insect control ingredient delivery device of claim 1, further comprising at least 0.05% by weight of kerosene.

4. The burnable insect control ingredient delivery device of claim 3, further comprising at least 0.05% by weight of peanut shell powder.

* * * * *